(12) United States Patent
Diekmann

(10) Patent No.: US 6,464,941 B1
(45) Date of Patent: Oct. 15, 2002

(54) BREATH ALCOHOL MEASURING APPARATUS HAVING A SAMPLE INTAKE CHANNEL AND A TEMPERATURE SENSOR MOUNTED THEREIN

(75) Inventor: Wilfried Diekmann, Lübeck (DE)

(73) Assignee: Dräger Sicherheitstechnik GmbH, Lübeck (DE)

(*) Notice: Subject to any disclaimer, the term of this patent is extended or adjusted under 35 U.S.C. 154(b) by 0 days.

(21) Appl. No.: 09/533,856

(22) Filed: Mar. 24, 2000

(30) Foreign Application Priority Data

Mar. 26, 1999 (DE) .......................... 199 13 783

(51) Int. Cl.[7] .............................................. G01N 33/48
(52) U.S. Cl. ...................... 422/84; 422/82.05; 422/93; 436/132; 436/900
(58) Field of Search .............................. 422/84, 93, 90, 422/98, 82.05; 436/132, 151, 900

(56) References Cited

U.S. PATENT DOCUMENTS

| | | | | |
|---|---|---|---|---|
| 3,858,573 A | * | 1/1975 | Ryan et al. ............ 128/205.12 |
| 4,090,078 A | * | 5/1978 | Heim ........................ 250/343 |
| 4,317,453 A | * | 3/1982 | Heim | |
| 4,391,777 A | * | 7/1983 | Hutson ...................... 250/343 |
| 5,017,018 A | * | 5/1991 | Luchi et al. ............... 250/346 |

OTHER PUBLICATIONS

"The Technical Concept for Evidential Breath Testing in Germany" by G. Schoknecht et al 13th International Conference on Alcohol, Drugs and Traffic Safety, Adelaide, 1995.

* cited by examiner

Primary Examiner—Lyle A. Alexander
(74) Attorney, Agent, or Firm—Walter Ottesen

(57) ABSTRACT

A breath alcohol measuring apparatus includes a sample intake channel (7) for receiving the respiratory gas sample and a temperature sensor mounted in the sample intake channel (7). The breath alcohol measuring apparatus is so improved that the influence of the mouthpiece on the detection of the temperature of the respiratory gas sample is substantially eliminated. The temperature sensor is configured as an infrared optical thermometer (14) with a filter (10) transmissive for the infrared radiation. The filter (10) is disposed in the sample intake channel (7).

8 Claims, 1 Drawing Sheet

BREATH ALCOHOL MEASURING APPARATUS HAVING A SAMPLE INTAKE CHANNEL AND A TEMPERATURE SENSOR MOUNTED THEREIN

BACKGROUND OF THE INVENTION

In known breath alcohol measuring apparatus, the alcohol concentration in the exhaled air is measured with indirect measuring methods, for example, via the electrochemical conversion of the alcohol molecules in a measuring cell, by infrared absorption or via the change of conductivity of a semiconductor. A conclusion as to the blood alcohol concentration can be drawn via empirical models of the and equilibrium and the kinetic of the mass transfer between the alcohol content of the blood and the alcohol concentration in the gas phase. The temperature of the gas phase and the temperature of the blood participate decisively in these empirical models. For example, the concentration of ethanol in the gas phase above an aqueous solution of ethanol changes by more than 6% per degree Kelvin.

In the context of field tests, measurements of test persons were carried out and differences in the respiratory gas temperature of up to 5.8 degrees Kelvin were determined. Such a temperature difference corresponds to a relative change of the equilibrium concentration of ethanol in the exhaled air of almost 40%. In known breath alcohol measuring apparatus, the temperature of the respiratory gas sample is measured in order to detect the fluctuations of the temperature of the respiratory gas and this temperature is used for corrective purposes.

A breath alcohol measuring apparatus is disclosed in the publication of G. Schoknecht et al entitled "The Technical Concept for Evidential Breath Testing in Germany", 13th International Conference on Alcohol, Drugs and Traffic Safety, Adelaide, Australia, Aug. 13 to 18, 1995. In the known breath alcohol measuring apparatus, a mouthpiece is seated in a preheated holder and a temperature sensor is disposed in the sample intake channel which is enclosed by the wall of the holder. Thermal elements or resistance temperature sensors are usually used as temperature sensors. The respiratory gas sample travels via the mouthpiece and a sample intake tube to a measuring chamber of an infrared measuring device.

It is disadvantageous in the known breath alcohol measuring apparatus that the respiratory gas sample exchanges heat with the mouthpiece at the location of the temperature measurement and this can lead to a change of the temperature measurement value by several degrees Kelvin. Especially large changes result when cold mouthpieces are used or when the construction of the mouthpiece is unfavorable, for example, with respect to material or wall thickness.

SUMMARY OF THE INVENTION

It is an object of the invention to provide a breath alcohol measuring apparatus of the type described above which is improved so that the influence of the mouthpiece on the measurement of temperature of the respiratory gas sample is substantially eliminated.

The breath alcohol measuring apparatus of the invention includes: a housing defining a sample intake channel for receiving a sample of respiratory gas from a test person; a filter disposed in the sample intake channel and being transmissive for infrared radiation emanating from the test person; and, a temperature sensor mounted downstream of the filter and the temperature sensor being an infrared optical thermometer.

The advantage of the invention is essentially that an infrared optical thermometer having a filter is used as the temperature sensor. The filter is permeable for infrared radiation and is mounted in the sample intake channel. The infrared optical thermometer evaluates the infrared radiation passing through the filter. The filter is positioned within the sample intake channel so that the infrared radiation, which is emitted from the mouth and/or throat area of the test person, is detected and thereby also the temperature of the oral cavity. The temperature of the oral cavity is significantly better suited for correcting the influence of temperature on the breath alcohol measurement than the temperature of the respiratory gas in the sample intake channel because the mass transfer between the respiratory air and the body tissue of the test person takes place almost exclusively on the path from the lung into the mouth region. The infrared radiation can be coupled out of the sample intake channel behind the filter with a simple collecting optic and be evaluated by the infrared optical thermometer. The infrared radiation path is so configured that no infrared radiation, which is reflected within the sample intake channel, reaches the thermometer. With the temperature measurement according to the invention, measuring accuracies in the order of magnitude of approximately 0.2 Kelvin are realized.

It is especially advantageous to arrange the filter within the sample intake channel perpendicular to the flow direction. Especially good temperature measuring results are achieved when the filter is located in the vicinity of the test person.

It is especially advantageous to place the filter directly in a mouthpiece connectable to the sample intake channel. For this purpose, the mouthpiece has a tubular inner part around which the respiratory gas sample flows. This inner part is closed by a wall piece formed as one piece on the inner part and is configured as a filter. With an appropriate selection of material, the mouthpiece as well as the filter can be injection molded from the same material such as polyethylene. Many other plastics can be used which are transmissive for infrared radiation.

An especially advantageous embodiment of the invention is to configure a membrane of a check valve, which is located in the mouthpiece, as a filter permeable for the infrared radiation. Check valves of this kind serve to prevent the test person from re-inhaling air already exhaled into the sample intake tube and are mostly anyway present so that no additional parts are needed. As a membrane, a material is selected which is permeable for infrared radiation in the wavelength range of interest.

The membrane of the check valve is configured as an infrared filter and can replace the filter located in the tubular inner part or can be provided additionally to this filter.

The infrared radiation passing through the filter is deflected onto the infrared optical thermometer by an aspherical mirror mounted in the sample intake channel.

BRIEF DESCRIPTION OF THE DRAWINGS

The single FIGURE (FIG. 1) of the drawing shows a schematic of the breath alcohol measuring apparatus according to an embodiment of the invention.

DESCRIPTION OF THE PREFERRED EMBODIMENTS OF THE INVENTION

Figure 1:
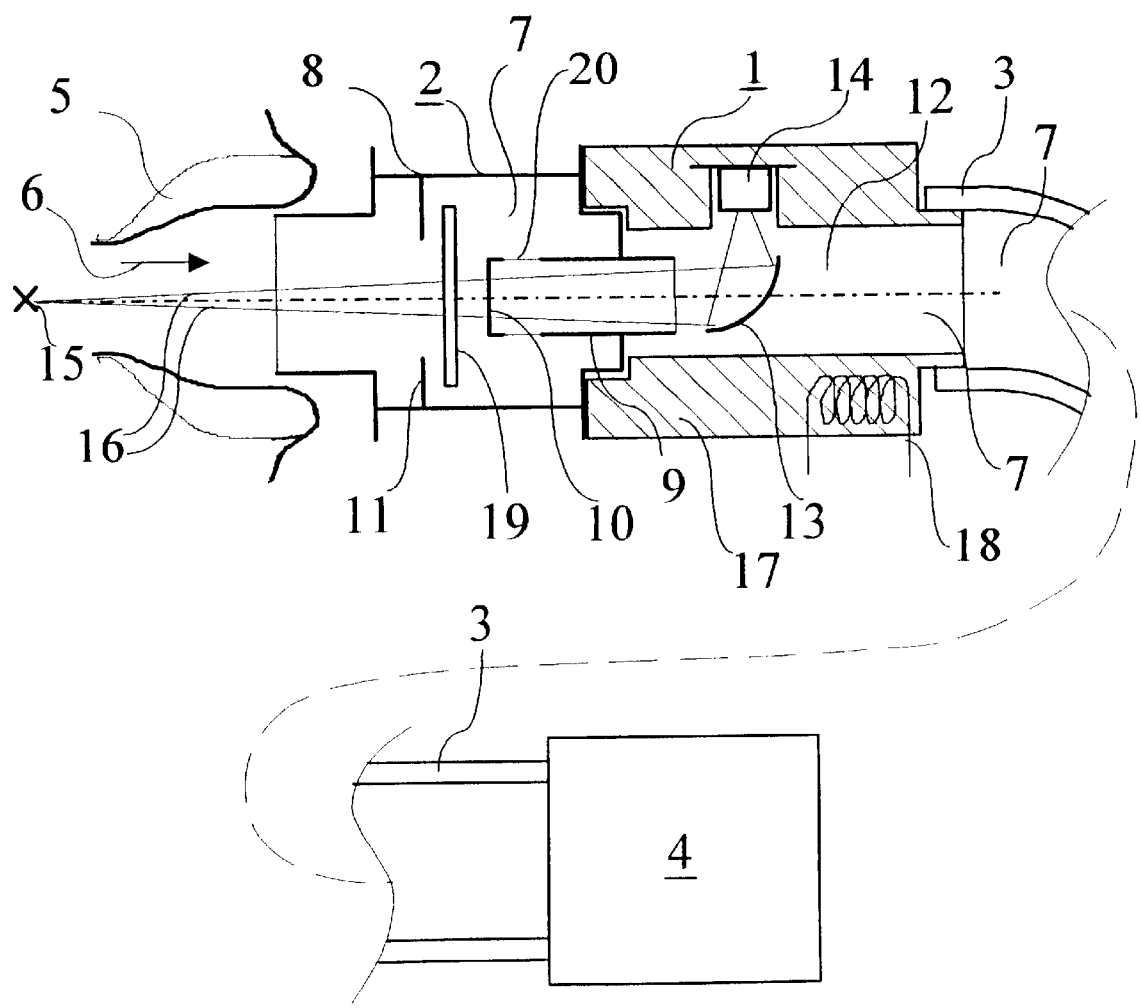

A mouthpiece 2 is seated in a holder 1 and a sample taking tube 3 is connected to the holder 1. The sample taking tube 3 is connected to a breath alcohol measuring apparatus 4.

When taking a sample, a test person 5 blows the respiratory gas sample, which is to be analyzed, in the throughflow direction (arrow 6) into a sample intake channel 7. The sample intake channel 7 extends from the mouthpiece 2 to the breath alcohol measuring device 4.

The mouthpiece 2 comprises a housing 8 having a tubular inner part 9 having an end whereat a filter 10 is mounted. The filter 10 is permeable to infrared radiation. The respiratory gas sample is conducted over a projection 11 and through openings 20 on the inner part 9 into an interior space 12 of the holder 1. The number of openings 20 is so selected that no significant resistance develops to exhaled air. The projection 11 is located on the housing 8. An aspherical mirror 13 and an infrared optical thermometer 14 are located in the interior space 12. The thermometer 14 is at right angles to the mirror 13. A region 15 of the oral cavity of the test person 5 is optically imaged on the thermometer 14 by the mirror 13.

The infrared beam path is shown schematically by lines 16. The filter 10 is so configured that it is transmissive for the infrared wavelength range emitted from the mucosa of the mouth. The mouthpiece 2 includes a movable membrane 19 to prevent backbreathing of respiratory gas from the sample intake channel 7. The membrane 19 lies against the projection 11 when the test person 5 draws or sucks on the mouthpiece 2 in a direction opposite to the arrow 6. The membrane 19 comprises a transparent material transmissive for infrared radiation.

The holder 1 includes a housing body 17 made of good thermal-conductive material. The housing body 17 has a heater 18 in order to heat up the inner space 12 to a temperature of approximately 38° C. so that condensation effects of the moisture saturated gas sample are prevented. The thermometer 14 is also located in the housing body 17. The temperature of a region 15 of the mouth interior of the test person 5 can be directly measured by the thermometer 14 without the surface temperature of the mouthpiece 2 and the temperature of the holder 1 affecting the measurement.

It is understood that the foregoing description is that of the preferred embodiments of the invention and that various changes and modifications may be made thereto without departing from the spirit and scope of the invention as defined in the appended claims.

What is claimed is:

1. A breath alcohol measuring apparatus comprising:
   a housing defining a sample intake channel for receiving a sample of respiratory gas from a test person;
   a filter disposed in said sample intake channel and being transmissive for infrared radiation;
   a temperature sensor mounted downstream of said filter and said temperature sensor being an infrared optical thermometer;
   said filter being so positioned within said sample intake channel that the infrared radiation, which is emitted from the mouth and/or throat area of the test person, is passed through said filter to said infrared optical thermometer; and,
   a breath alcohol measuring unit operatively connected to said intake channel downstream of said temperature sensor.

2. The breath alcohol measuring apparatus of claim 9, said sample intake channel defining a flow direction and said filter being essentially perpendicular to said flow direction.

3. The breath alcohol measuring apparatus of claim 1, said housing including a holder and a mouthpiece connectable to said holder; said holder and said mouthpiece conjointly defining said sample intake channel; and, said filter being mounted in said mouthpiece.

4. The breath alcohol measuring apparatus of claim 3, said mouthpiece having an interior passage defining a portion of said sample intake channel; said mouthpiece further having a tubular inner part mounted in said passage and through which said sample of respiratory gas flows; and, said tubular inner part having an end wall defining said filter and said end wall being formed as an integral part of said tubular inner part.

5. The breath alcohol measuring apparatus of claim 3, further comprising a check valve mounted in said mouthpiece upstream of said infrared optical thermometer; and, said check valve having a membrane defining said filter transmissive for infrared radiation.

6. The breath alcohol measuring apparatus of claim 2, wherein said infrared optical thermometer is disposed laterally of said flow direction.

7. The breath alcohol measuring apparatus of claim 6, wherein said means is an aspherical mirror mounted downstream of said filter.

8. A breath alcohol measuring apparatus comprising:
   a housing including a holder and a mouthpiece connectable to said holder; said holder and said mouthpiece conjointly defining a sample intake channel for receiving a sample of respiratory gas from a test person;
   said sample intake channel defining a flow direction for said sample;
   a check valve mounted in said mouthpiece;
   said check valve including: a stop formed in said mouthpiece and defining a through opening for passing said sample of respiratory gas; and, a valve member essentially perpendicular to said flow direction and being movably mounted in said sample intake channel for movement between a first position displaced from said stop when the test person blows into said mouthpiece and a second position against said stop when the test person back breathes thereby preventing the test person from withdrawing exhaled air from said apparatus;
   said valve member being a membrane transmissive for infrared radiation emanating from the oral cavity of the test person;
   a filter disposed downstream of said membrane in said sample intake channel and being transmissive for said infrared radiation; a temperature sensor mounted downstream of said filter and said temperature sensor being an infrared optical thermometer;
   said filter being so positioned within said sample intake channel that the infrared radiation, which is emitted from the mouth and/or throat area of the test person, is passed through said filter to said infrared optical thermometer; and,
   a breath alcohol measuring unit operatively connected to said intake channel downstream of said temperature sensor.

\* \* \* \* \*

UNITED STATES PATENT AND TRADEMARK OFFICE
CERTIFICATE OF CORRECTION

PATENT NO.   : 6,464,941 B1
DATED        : October 15, 2002
INVENTOR(S)  : Wilfried Diekmann It is certified that error appears in the above-identified patent and that said Letters Patent is hereby corrected as shown below:

<u>Column 3,</u>
Line 63, delete "claim 9" and substitute -- claim 1 -- therefor.

Signed and Sealed this

Eleventh Day of March, 2003

JAMES E. ROGAN
*Director of the United States Patent and Trademark Office*